(12) United States Patent
Melo Sant'anna et al.

(10) Patent No.: US 8,232,082 B2
(45) Date of Patent: Jul. 31, 2012

(54) PROCESS FOR THE FERMENTATIVE PRODUCTION OF ETHANOL FROM SOLID LIGNOCELLULOSIC MATERIAL COMPRISING A STEP OF TREATING A SOLID LIGNOCELLULOSIC MATERIAL WITH ALKALINE SOLUTION IN ORDER TO REMOVE THE LIGNIN

(75) Inventors: Lidia Maria Melo Sant'anna, Niteroi (BR); Nei Pereira, Jr., Rio de Janeiro (BR); Absai Da Conceicao Gomes, Rio de Janeiro (BR); Mariana Penuela Vasques, Rio de Janeiro (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 403 days.

(21) Appl. No.: 12/297,088

(22) PCT Filed: Nov. 30, 2007

(86) PCT No.: PCT/GB2007/004618
§ 371 (c)(1),
(2), (4) Date: Jul. 8, 2009

(87) PCT Pub. No.: WO2008/065433
PCT Pub. Date: Jun. 5, 2008

(65) Prior Publication Data
US 2010/0035318 A1 Feb. 11, 2010

(30) Foreign Application Priority Data

Nov. 30, 2006 (BR) ...................................... 0605017

(51) Int. Cl.
*C12P 7/10* (2006.01)
(52) U.S. Cl. ....................................................... 435/165
(58) Field of Classification Search .................. 435/165
See application file for complete search history.

(56) References Cited

U.S. PATENT DOCUMENTS 5,628,830 A 5/1997 Brink
7,604,967 B2 * 10/2009 Yang et al. .................... 435/161

FOREIGN PATENT DOCUMENTS

BR PI 0505299 A 8/2007
WO 01/32715 A 5/2001

* cited by examiner

*Primary Examiner* — Herbert J Lilling
(74) *Attorney, Agent, or Firm* — Sughrue Mion, PLLC

(57) ABSTRACT

The present invention relates to a process for obtaining fuel ethanol by using agricultural and agroindustrial waste materials composed of lignocellulose, and especially sugar cane bagasse. These residues have significant contents of carbohydrates in the form of polysaccharides (cellulose and hemicellulose), which can be hydrolyzed by chemical and enzymic processes. The hemicellulose fraction is submitted to mild hydrolysis with sulphuric acid, and the solid material from this hydrolysis is submitted to a process of saccharification (enzymic hydrolysis) with simultaneous rapid alcoholic fermentation under conditions which allow a significant increase in conversion to alcohol in a greatly shortened time.

19 Claims, 2 Drawing Sheets

PROCESS FOR THE FERMENTATIVE PRODUCTION OF ETHANOL FROM SOLID LIGNOCELLULOSIC MATERIAL COMPRISING A STEP OF TREATING A SOLID LIGNOCELLULOSIC MATERIAL WITH ALKALINE SOLUTION IN ORDER TO REMOVE THE LIGNIN

FIELD OF THE INVENTION

The present invention relates to a process for obtaining fuel ethanol by using lignocellulose agricultural and agroindustrial waste products, and especially sugar cane bagasse. These residues have significant contents of carbohydrates in the form of polysaccharides (cellulose and hemicellulose), which can be hydrolysed by chemical and enzymic processes. The hemicellulose fraction is submitted to mild hydrolysis with sulphuric acid, and the solid material from this hydrolysis is submitted to a process of saccharification (enzymic hydrolysis) with simultaneous rapid alcoholic fermentation under conditions which allow a significant increase in conversion to ethanol in a greatly shortened time.

1. Basis of the Invention

Wastes with a lignocellulose composition from agricultural and agroindustrial activities are a major environmental problem; however, they can be valuable sources of low-cost renewable starting materials for producing a variety of chemicals and fuels, such as ethanol.

In order to make use of the polysaccharide fractions for ethanol production, these fractions need to be efficiently hydrolysed.

These polysaccharides are fractionated by means of a pretreatment which consists of a reaction known as acid hydrolysis, with the objective of hydrolyzing the hemicellulose fraction. The solid product from this step, which is rich in cellulose, still needs to be treated in order to remove the soluble lignin under alkaline conditions so as to guarantee access of the enzymes to the cellulosic fibres.

Conversion of cellulose to ethanol involves two basic steps: hydrolysis of the long chains of the cellulose molecules to give sugars (hexoses), and fermentation of these sugars to give ethanol. In nature, these processes are carried out by fungi and bacteria, which secrete enzymes capable of hydrolysing cellulose (cellulases), and principally by yeasts in the case of fermentation of sugars to ethanol. The concept of the present application is consistent with the natural processes.

This strategy eliminates the presence of toxins, which would be produced by chemical hydrolysis of cellulose, and minimizes inhibition of enzymes of the cellulose complex by the products of hydrolysis itself (glucose and cellobiose). This technique is termed the SSF process ("simultaneous saccharification and fermentation") and involves enzymic hydrolysis and simultaneous ethanolic fermentation.

2. Related Art

Concern with conserving the environment is increasing daily. In this context, use of agricultural and agroindustrial waste products and the search for replacement and/or alternative products which are less harmful to nature are important topics worldwide. With the same idea in mind, there is a search for alternative energy sources, and use of agricultural and agroindustrial waste products which could produce economically viable products and/or result in products that are less polluting. In the field of alternative sources, many attempts have been made to produce cleaner fuels, such as ethanol, for example.

In Brazil, the growth of the sugar ethanol industry, and consequent production of large quantities of excess sugar cane bagasse, has given rise to a very promising scenario, in view of the necessity to make rational use of this lignocellulose material.

Owing to environmental and economic interests, the use of ethanol as a fuel added to gasoline or as starting material for biodiesel manufacture has grown vertiginously, with Brazil being one of the world's largest producers. As a result, Brazil produces enormous quantities of bagasse, and also sugar cane straw, both of which have considerable potential for biotechnological ethanol production.

Production of ethanol from sugar cane bagasse by enzymic and fermentative routes will enable the use of an underused material to produce a product which is of enormous industrial interest, with economic and environmental gains.

The simultaneous saccharification and fermentation technique (SSF process) directed towards using the cellulose fraction has been described in the specialist literature and has been applied for various purposes for producing chemicals and fuels. However, it has yet to be implemented on a commercial scale.

The principal difficulty which needs to be overcome relates to the microorganism, which needs to be resistant to the operating conditions, especially as regards concentrations of inhibitors generated in the reaction medium, such as furfural, hydroxymethyl-furfural, heavy metals, terpenes, tannins and phenol compounds, etc., for example, resulting from the pretreatment of the lignocellulose material, which inhibit the growth of the yeast.

Another difficulty inherent to biological agents is their limitation as regards utilization of carbohydrates resulting from the processes of hydrolysis (pentoses and hexoses). The association of these two factors leads to long fermentation processes, resulting in a low volume production rate, which is a parameter of fundamental importance as regards transfer to industrial scale.

The great majority of recent reports describe the use of genetically modified microorganisms developed for a specific application, designed to avoid these problems.

Ethanol production by biological techniques has been under study for a long time; however, it has had a considerable boost in recent years. As mentioned previously, the great obstacle to be overcome relates to the production rate, namely, to achieve an economically viable process which gives good yields using easily accessible starting materials.

Grohmann et al. (U.S. Pat. No. 5,125,977) describe a process in which biomass (agricultural, forestry, plant and food processing waste) is pretreated in two steps to recover xylose. In the first step, hemicellulose, basically containing xylanes, is pre-hydrolysed with dilute acid (sulphuric acid 9% v/v), and the residue is submitted to a second step of enzymic hydrolysis, leaving the biomass to react for sufficient time for the cellulose to be slowly hydrolysed. The objective of the process is to recover the xylane such that ca. 90% can be hydrolysed, avoiding the limitations of conventional processes for producing xylose. The drawback of the method is that when harsh temperature conditions are used (160° C. to 220° C.) many substances are formed which inhibit the metabolism of the majority of microorganisms used in fermentation processes.

Patent document GB 2,253,633, which corresponds to Brazilian Patent PI 9200100 of 15 Jan. 1992, describes a process for producing ethanol from biomass in which the substrate includes a hydrolysate of cellulose, hemicellulose and starch, with the objective of producing fermentable six-carbon sugars. The fermentation uses a genetically modified yeast strain (*Brettanomyces custersii* CBS 5512), which produces the enzyme β-glucosidade, enabling this yeast to ferment both glucose and cellobiose. However, the problem of fermenting pentoses remains unsolved.

U.S. Pat. No. 5,231,017 describes a process for producing ethanol using starting material with a high solids content, such as maize cobs, grains, cereals and mixtures thereof. The starch present in these starting materials is brought into contact with a commercial α-amylase from *Bacillus lickenformis* (TAKA-THERM II®), to give a fermentable liquid medium, which is saccharified in the presence of commercial glucoamylase derived from *Aspergillus niger* (DISTILLASE®) to obtain hydrolysed starch and sugars, which are fermented by the yeast *Saccharomyces cerevisae* to obtain ethanol. Although it uses the technique of simultaneous saccharification and fermentation, this method cannot be applied to sugar cane bagasse.

Torget et al, (U.S. Pat. No. 5,705,369) describe a generic process for pre-hydrolysis of lignocellulose material, in which different combinations of ranges of temperature and reaction time are investigated with the aim of obtaining better percentage separation of hemicellulose and lignin from cellulose. Different temperatures (in the range 120° C. to 240° C.) and pH (in the range 1-7) were tested in a system in which the fluid (soluble products of pre-hydrolysis) move through the solid phase ("flow-through" system) and the quantities of xylane and lignin extracted from the material were determined. A combination of less severe conditions gave an increase of 5% in removal of lignin.

Brazilian Patent Application PI 0600409-1 of 8 Feb. 2006 describes a process for producing cellulolytic and hemicellulolytic enzymes from waste materials (hard woods and cereal straw). These waste materials are used as a carbon source to induce these enzymes, with genetically improved and recombined strains of *Trichoderma reesei*. In the presence of an inducing substrate (cellulose for example) wild strains of this microorganism can secrete the complex considered most apt for cellulose hydrolysis. It is thus a process for producing cellulolytic and/or hemicellulolytic enzymes produced by a special strain. The first, pretreatment, step comprises expansion in steam (150° C. to 250° C.) under acid conditions for several minutes, in order to convert the hemicellulose into monomers, with xylose being the predominant sugar. The sugars are extracted by washing with the aqueous phase, and used as a carbon source for enzyme production; the solid residue from the extraction, which contains cellulose and lignin, can be hydrolysed by the cellulolytic enzymes produced.

The object of the invention in the present application, which will be described in detail below, is also the use of lignocellulose waste, and more particularly solid sugar cane bagasse which has been pretreated by the process for acid hydrolysis of hemicellulose in Brazilian Patent Application PI 0505299-8 of 11 Nov. 2005 by the same applicant.

SUMMARY OF THE INVENTION

The present invention relates to a process for obtaining fuel ethanol by using lignocellulose material by the technique of rapid simultaneous saccharification and fermentation under specific conditions which give better use of the cellulose fraction and efficient ethanol production.

More specifically, the process of the invention comprises treatment of the solid residue after acid hydrolysis of sugar cane bagasse. According to this process, a hydrolysate of the hemicellulose fraction of sugar cane bagasse, rich in xylose, was obtained by mild hydrolysis with dilute sulphuric acid, and fermented using a strain of the yeast *Pichia stipitis* suitably acclimatized to the principal substrate in the hydrolysate (xylose). The solid residue from the acid hydrolysis (cellulolignin) was treated still within the reactor in order to remove lignin by means of a series of alkaline rinses in order to prepare the cellulose fibres to receive a suitable commercial enzyme preparation. The partially delignified material was submitted to rapid saccharification and fermentation, to produce ethanol, in the presence of a strain of a naturally occurring yeast of the species *Saccharomyces cerevisiae*.

The great advantage of this process is that ethanol can be obtained from sugar cane bagasse, achieving high volume production rates varying from 1 to 3 g/L.h, realizing all of the metabolic potential of a naturally occurring yeast without the need for genetic modification.

DETAILED DESCRIPTION OF THE INVENTION

The object of the present invention is to make use of the polysaccharide fractions of sugar cane bagasse, which can be used for producing ethanol, as a fuel or gasoline additive, or as a chemical starting material, without using high enzyme concentrations, and operating with a short period of saccharification and alcoholic fermentation.

Figure 1:
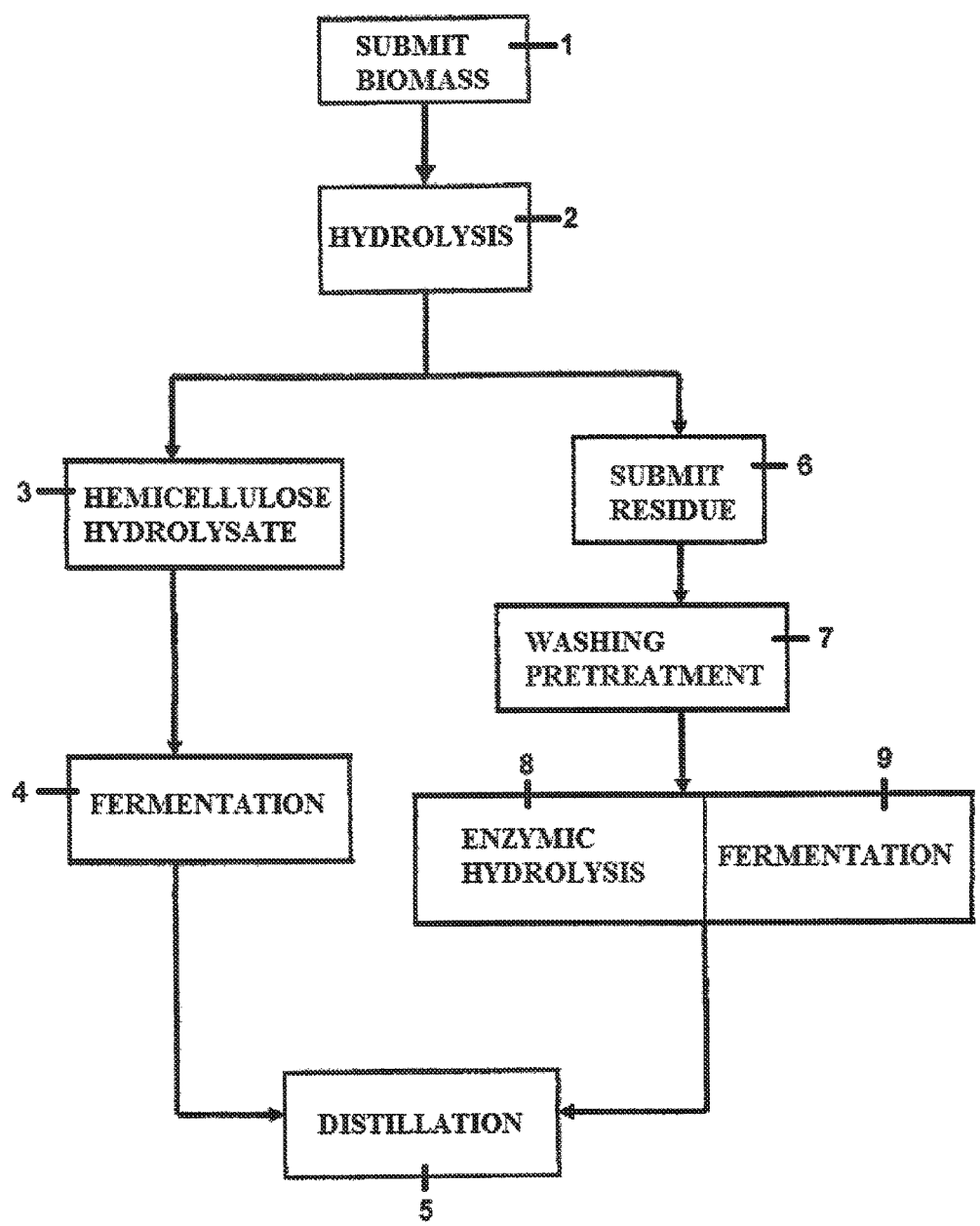
FIG. 1 is a simplified flow diagram of the principal steps of the process of the invention.

In order to better appreciate the invention, it is described with reference to the flow diagram in FIG. 1, which shows a preferred embodiment of the invention. As indicated in FIG. 1, biomass (1) containing lignocellulose material is initially submitted to a process of hydrolysis with dilute acid (2), which gives a hemicellulose hydrolysate (3) rich in pentoses, which is fermented (4) to produce ethanol, which is later distilled (5), and a solid residue (6) rich in cellulose and lignin—cellulolignin. This residue (6) is submitted to pre-treatment by washing (7) with an alkaline solution, and later to a process of enzymic hydrolysis (saccharification) (8) to release glucose, and simultaneously to a process of fermentation (9) with yeast, to ferment the glucose to ethanol, which is separated from the fermented medium and distilled (5).

The first stage of the process comprises mild hydrolysis of the sugar cane bagasse with 1% sulphuric acid in order to preferentially obtain pentoses, and especially xylose, the principal constituent of the hemicellulose fraction of sugar cane bagasse.

This first stage is described in detail in Brazilian Patent Application PI 0505299-8, filed by the same applicant. The cellulose material is homogenized and submitted to mild acid hydrolysis in a special press reactor, within which the main vessel is at a pressure of 1 atm (corresponding to a temperature of 121° C.) for a duration that is decided to suit the solid:liquid ratio, and normally in the range from 30 to 50 minutes. The liquid phase (hydrolysate) is separated from the solid residue by pressing still within the reactor, and submitted to a process of fermentation in the presence of Pichia stipitis yeast acclimatized and adapted to the fermentation medium, to obtain ethanol.

However, the solid residue still contains a high level of cellulose, which needs to be hydrolysed to sugars, which are fermented by a strain of *Saccharomyces cerevisiae* to produce ethanol. The process which is the object of the present invention, which corresponds to the second stage of the overall process, will be described from this point onwards.

The second stage of the process basically comprises the treatment of the solid residue, namely:
a) pretreatment of the cellulolignin in an alkaline medium, followed by washing with water;
b) transfer of the residue to a bioreactor for enzymic hydrolysis (saccharification) of the same at moderate temperature, in the presence of a commercial enzyme load for a period preferably from 8-12 hours;
c) simultaneous fermentation of the cellulose fraction of the material hydrolysed in the preceding step, by adding a yeast suited to production of ethanol, maintaining the enzyme concentration, for a maximum period of 32 hours;
d) separation and distillation of the ethanol produced.

The principal advantage of the process of the present invention is that it achieves ethanol production at a significant volume production rate in decreased time, due to tested and optimized conditions, resulting in economic gains which make commercial implementation thereof viable.

The known processes in the prior art do not achieve conversion to ethanol in such short times, despite using genetically modified microorganisms, and require ca. 3-5 days. With the process of the invention, maximum production of ethanol is already found after only 8 hours of saccharification and an additional 32 hours of fermentation.

The efficiency of the process is attributed to the rigorous control of the determinant variables involved in the same, and the determination of optimal operating conditions.

In order to better evaluate the process of the invention, a preferred embodiment of the process will be described; however, the examples are presented merely by way of illustration.

Preferred Mode for Carrying Out the Invention

As mentioned previously, the first step of the process involves acid hydrolysis of the lignocellulose material in order to obtain a hemicellulose hydrolysate and a solid fraction. The method adopted is summarized in Example 1 below.

EXAMPLE 1

The first step of the process is hydrolysis with sulphuric acid (1% v/v) to obtain a hemicellulose hydrolysate and a solid fraction, and acid hydrolysis of the hemicellulose fraction for about 40 minutes, using an optimal solid:liquid ratio. The solid material is removed by pressing in a press reactor specially developed for the process in PI 0502599-8. The hydrolysate is neutralized with $Ca(OH)_2$ and filtered, with the liquid hydrolysate being removed to be submitted to fermentation of the pentoses by an acclimatized biomass which is used at a concentration of 10 g/L, in a bioreactor for 20-30 h, at a temperature of approximately 30° C. The biomass was acclimatized by sequential cell propagation, with the content of hydrolysate being gradually increased. At the end of the fermentation the ethanol is separated and distilled.

The volume production rate obtained was of the order of 1.0 g/L.h.

EXAMPLE 2

The solid separated in the reactor as described in the previous example is treated in accordance with the process of the invention. The solid from this step, which is rich in cellulose, is submitted to a series of alkaline washes while still within the press reactor, in order to partially remove the soluble lignin, the aromatic constituents of which inhibit the fermentation process. This step is of fundamental importance in as much as it increases the accessibility of the cellulose fibres to the enzymes.

The solid residue separated by pressing in the reactor is washed with an alkaline solution (NaOH 4% w/v) and then submitted to successive washes with slightly acidified (HCl) water until reaching pH 6-7, and is fed back to the bioreactor for enzyme pretreatment. In the bioreactor, the solid residue is mixed with water containing micronutrients in the ratio 1:10-20, while maintaining a temperature in the range 30° C. to 50° C., and preferably 47° C., with commercial cellulose enzymes (GENENCOR® GC220) being added to this mixture at concentrations of 20-30 FPU/g, and the reaction being allowed to proceed for 8 to 12 h. This is followed by simultaneous fermentation of the fermentation medium, with microorganisms being added which have activity suited to ethanol production—*Saccharomyces cerevisae*, without any genetic modification. The temperature in the reactor is maintained in the range 30° C. to 39° C., and preferably close to 37° C., with the concentration of yeast cells being maintained in the range 2 to 6 g/L, for a maximum period of 30 to 32 hours.

Conversion of cellulose to ethanol involves two fundamental steps: hydrolysis of the long chains of the cellulose molecules to sugars (hexoses), and fermentation of these sugars to ethanol.

Elimination of the toxic substances which would be generated by chemical hydrolysis of cellulose minimizes inhibition of enzymes of the cellulase complex by their own products of hydrolysis (glucose and cellobiose). The process of the present invention also uses the technique of simultaneous saccharification and fermentation, known in the art as the SSF process.

Concentrations of ethanol between 50 and 55 g/L were obtained, and the productivity rate achieved was in the range 1.5 to 2.0 g/L.h.

Figure 2:
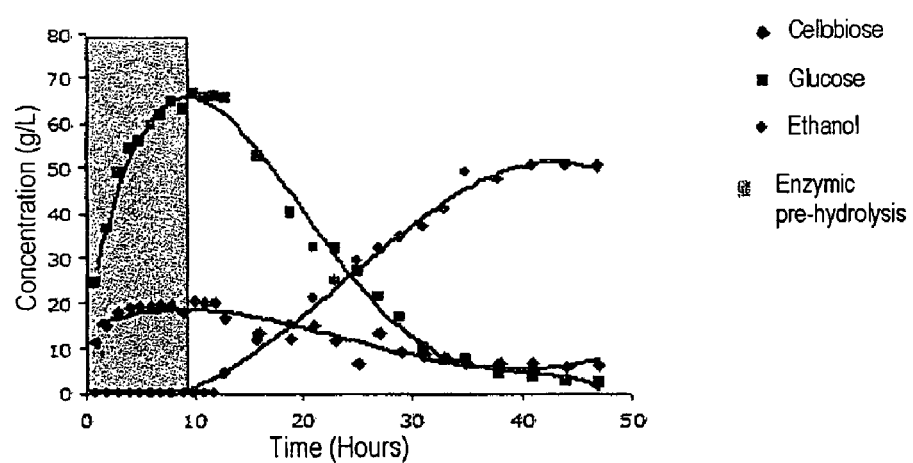
FIG. 2 is a graph illustrating results obtained with the process of the invention.

The results are presented in the graph of concentration against time shown in FIG. 2.

When both stages of the process were applied, conversion to ethanol reached 182 L/tonne of sugar cane bagasse, which makes the process as a whole considerably economically viable, given that it is possible to decrease the time for conversion in the second stage from 4-5 days to 32 hours.

It should be emphasised, however, that the examples presented here are merely illustrative in nature and do not limit the invention, and it will be evident to those skilled in the art that other enzyme preparations, commercial or otherwise, and different yeasts, can be employed within the scope of the invention.

The invention claimed is:
1. A process for producing ethanol enzymically from lignocellulose material, which process comprises the steps of:
a) submitting a solid material comprising cellulose and lignin to one or more washes with alkaline solution at least partially to remove the lignin from said solid material, washing with water, and separating the remaining solid material from the aqueous phase; then
b) hydrolysing the solid material, comprising reacting the solid material with a solution of micronutrients and a cellulolytic enzyme, wherein the solid:liquid ratio is from 1:10 to 1:20, the temperature is from 30° C. to 50° C., the enzyme concentration is from 20-30 FPU/g, and the reaction is allowed to proceed for from 8-32 hours; and
c) fermenting, the medium resulting from enzymic hydrolysis, comprising adding an ethanol-producing yeast, wherein the yeast has a cell concentration of from 2 to 6 g/L, and maintaining a temperature of from 30° C. to 39° C., for a period of not more than 32 hours; then
d) separating of the ethanol by distillation.

2. The process according to claim 1, wherein the yeast is non genetically-modified *Saccharomyces cerevisae* yeast.

3. The process according to claim 1, wherein the production rate of the process is in the range 1.0 to 3.0 g/L.h.

4. The process according to claim 1, wherein the total period of the process is not more than 32 h.

5. The process according to claim 1, wherein the hydrolysis is conducted at a temperature of from 45° C. to 49° C.

6. The process according to claim 1, wherein the fermentation is conducted at a temperature of 35° C. to 39° C.

7. The process according to claim 1, wherein the concentration of biomass of the yeast of step c) is maintained in the range of from 2 to 6 g/L.

8. The process according to claim 1, wherein the enzyme referred to in step b) is provided by adding a commercial cellulose enzyme preparation.

9. The process according to claim 1, wherein the lignocellulose material comprises sugar cane bagasse.

10. The process according to claim 1, in which simultaneous saccharification and fermentation (SSF) is carried out.

11. A process for producing ethanol enzymically from lignocellulose material, which process comprises the steps of:
   i) hydrolysing and fermenting lignocellulose material, and retaining the solid material; and
   ii) performing the process according to claim 1 on said solid material.

12. The process according to claim 1, wherein the washing with water in step a) is conducted with acidified water to produce a PH of from 6 to 7.

13. The process according to claim 1, wherein the step of separating the remaining solid material from the aqueous phase in step a) is done by means of filtration in a special or other press reactor.

14. The process according to claim 13, wherein the step b) of hydrolysing the solid material is carried out while still in the reactor.

15. The process according to claim 1, wherein the step b), the reaction is allowed to proceed for from 8-30 hours.

16. The process according to claim 15, wherein the reaction is allowed to proceed for from 8 to 12 hours.

17. The process according to claim 1, wherein the fermenting step c) is conducted by simultaneous fermentation.

18. The process according to claim 1, wherein the step c) the temperature of from 30° C. to 39° C. is maintained for a period of 30 to 32 hours.

19. The process according to claim 11, wherein the lignocellulose material is sugar cane bagasse.

* * * * *